US012605129B2

(12) United States Patent     (10) Patent No.:    US 12,605,129 B2
Pavel et al.             (45) Date of Patent:      Apr. 21, 2026

---

(54) MOBILE MEDICAL DEVICE

(71) Applicant: Siemens Healthcare GmbH, Erlangen (DE)

(72) Inventors: Zsolt Pavel, Poxdorf (DE); Norbert Scherer, Pinzberg (DE)

(73) Assignee: Siemens Healthineers AG, Forchheim (DE)

( * ) Notice: Subject to any disclaimer, the term of this patent is extended or adjusted under 35 U.S.C. 154(b) by 224 days.

(21) Appl. No.: 18/218,198

(22) Filed: Jul. 5, 2023

(65) Prior Publication Data

US 2024/0008830 A1     Jan. 11, 2024

(30) Foreign Application Priority Data

Jul. 5, 2022    (DE) ..................... 10 2022 206 844.0

(51) Int. Cl.
*A61B 6/00*        (2024.01)
(52) U.S. Cl.
CPC ................................. *A61B 6/4405* (2013.01)
(58) Field of Classification Search
CPC ... A61B 6/4405; A61B 6/4441; A61B 6/0407; A61B 6/035; A61B 5/055; A61B 6/032; A61B 6/4411; A61B 6/4447; A61B 6/467; A61B 6/547; A61B 6/04; A61B 6/4435; A61B 6/4417; A61B 6/4488; A61B 6/037; A61B 50/13; A61B 2560/0214; A61B 2560/0431; A61B 2560/0437; A61B 5/0046; A61B 5/0555; A61B 6/548; B60B 19/12; B60B 11/02; B60B 19/003; B60B 19/125; B60B 33/0028; B60B 33/0042; B60B 33/0044;

B60B 33/0052; B60B 33/045; B60B 2200/26; B60B 2900/531; B60G 11/36; B60G 3/20; B60G 15/067; B60G 3/202; B60G 3/22; B60G 7/001;

(Continued)

(56) References Cited

U.S. PATENT DOCUMENTS

| | | | | |
|---|---|---|---|---|
| 5,323,867 A | * | 6/1994 | Griffin | ................. B25J 11/0025 |
| | | | | 180/22 |
| 2011/0001301 A1 | * | 1/2011 | Li | .......................... B60G 11/18 |
| | | | | 280/124.167 |

(Continued)

FOREIGN PATENT DOCUMENTS

| | | |
|---|---|---|
| CN | 214712572 U | 11/2021 |
| DE | 102015218487 A1 | 3/2017 |

(Continued)

OTHER PUBLICATIONS

Wikipedia—"Mecanum Wheel" https://en.wikipedia.org/wiki/Mecanum_wheel. pp. 1-4. Obtained Jun. 29, 2022.

*Primary Examiner* — Irakli Kiknadze
(74) *Attorney, Agent, or Firm* — Lempia Summerfield Katz LLC

(57) ABSTRACT

For particularly good maneuverability, a mobile medical device is provided with a device carrier. The device carrier includes at least three wheels, of which at least two are motor-drivable omnidirectional wheels. At least two of the omnidirectional wheels are arranged in pairs on opposite sides of a chassis of the device carrier using a wheel suspension in each case. The wheel suspension is formed by a double wishbone wheel suspension.

12 Claims, 5 Drawing Sheets

(58) Field of Classification Search
 CPC ...... B60G 2200/1442; B60G 2200/182; B60G
 2200/422; B60G 2200/462; B60G
 2202/312; B60G 2204/182; B60G
 2300/50; B60G 3/28; B62D 63/02; B62D
 63/04; G01S 17/88; F16C 25/083; F16C
 19/547; F16C 19/364; F16C 33/784;
 F16C 13/006; F16C 13/022; F16C
 13/003; F16C 2240/34; F16C 2240/70;
 F16C 2240/26; F16C 2316/10; Y02T
 10/70; B60K 1/04; B60K 7/0007; B60K
 2001/0416; B60K 2001/0438; B60K
 2007/0038; B60K 2007/0061; H01M
 10/0525; A61G 1/0243; A61G 7/0528;
 A61G 1/0268; A61G 1/0275; A61G
 1/0281
 USPC ........................................................ 378/198
 See application file for complete search history.

(56) References Cited

U.S. PATENT DOCUMENTS

| | | |
|---|---|---|
| 2014/0265182 A1 | 9/2014 | Stanton et al. |
| 2018/0242932 A1 * | 8/2018 | Sullivan ................ A61B 6/547 |
| 2020/0016927 A1 | 1/2020 | Dietrich |
| 2021/0345977 A1 | 11/2021 | Kumar |

FOREIGN PATENT DOCUMENTS

| | | | |
|---|---|---|---|
| DE | 102018211669 A1 | | 1/2020 |
| JP | 2014024434 A | | 2/2014 |
| JP | 5762367 B2 | * | 8/2015 |
| JP | 2019209896 A | | 12/2019 |
| JP | 2021176505 A | | 11/2021 |

* cited by examiner

MOBILE MEDICAL DEVICE

This application claims the benefit of German Patent Application No. DE 10 2022 206 844.0, filed on Jul. 5, 2022, which is hereby incorporated by reference in its entirety.

BACKGROUND

The present embodiments relate to a mobile medical device with a device carrier.

Mobile X-ray devices in the form of C-arm devices are, for example, used for intraoperative imaging when deployed in surgical procedures. Herein, the mobile X-ray devices are to be positioned precisely in relation to the patient to be treated before each procedure. It is known to equip the devices with wheels on which the devices may be moved manually. It is furthermore known to drive the wheels in a motorized manner in order to enable the devices to be moved with less or no exertion of force and to automate certain movements of the devices for clinical applications.

DE 10 2015 218 487 A1 discloses a C-arm X-ray device that has a device carrier with at least three wheels. For good maneuverability, at least two of the wheels are configured as omnidirectional wheels.

New applications also employ C-arm X-ray devices with four motor-operated omnidirectional wheels and, for example, also mecanum wheels in order to be able to travel flexibly in all directions with every revolution. With such an arrangement, these wheels are to have permanent contact with the ground in order to be able to implement the correspondingly required maneuvers with high reliability and precision. However, if the ground is uneven, it may be the case that at times only three of the four wheels remain in contact with the ground. As a result of this, precise and reliable movement and positioning of the device in all possible directions with each revolution of the wheels is no longer possible.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a mobile medical device and, for example, a C-arm X-ray device with omnidirectional wheels that provides reliable maneuvering on all types of ground are provided.

In the mobile medical device according to the present embodiments with a device carrier, the device carrier includes at least three (e.g., four) wheels, of which at least two are motor-driven omnidirectional wheels. At least two of the omnidirectional wheels are arranged in pairs on opposite sides of a chassis of the device carrier using a wheel suspension in each case. The wheel suspensions are formed by double wishbone wheel suspensions. In omnidirectional wheels, it is important for the running surface consisting of rollers to have reliable ground contact for the entire running surface. However, simple solutions such as, for example, a spring in the axle or a flexible rubberized wheel contact surface are not sufficient since then only part of the running surface and thus of the rollers of the wheel are in contact with the ground, or the rollers of the wheel are covered. The double wishbone wheel suspensions enable a constant pressure to be consistently exerted on the floor in a simple manner, even in the case of uneven floors, hence preventing the individual rollers in the omnidirectional wheels from losing traction with the floor. Providing full contact between the omnidirectional wheels and the floor causes the motorized drive to function reliably and provides exact and advantageous maneuverability of the omnidirectional wheels using the rollers. Hence, the medical device with the omnidirectional wheels may also be deployed on uneven ground, thus enabling use to be made of its improved image quality and diagnostic capabilities.

In one embodiment, for particularly good stability of the device, the mobile medical device has four motor-driven omnidirectional wheels. According to one embodiment, in each case, two of the four motor-driven omnidirectional wheels are arranged in pairs on opposite sides of a chassis of the device carrier using a double wishbone wheel suspension in each case. The fact that each wheel has its own double wishbone wheel suspension provides continuous floor contact for all four individually driven omnidirectional wheels, thus providing precise movement with every revolution.

According to a further embodiment, each wheel suspension has at least one (e.g., two) spring suspension elements. In this way, the device and its sensitive components are protected against damage from impacts even on an uneven floor. This significantly reduces wear on the components. The spring suspension elements may, for example, be configured as springs. Springs are readily available, inexpensive, and reliable.

In one embodiment, the device is configured as a mobile C-arm X-ray device. Mobile C-arm X-ray devices may be used for 2D-imaging, 3D-imaging, and tomosynthesis and are versatile in many areas of application. Their mobility enables the mobile C-arm X-ray devices to be used not only in operating theaters, but also in other locations for diagnosis and therapy support.

According to a further embodiment, the double wishbone wheel suspensions in each case have an upper wishbone and a lower wishbone that may be arranged parallel to one another. Each of the upper wishbone and the lower wishbone may, for example, be connected at two points to the chassis of the device carrier and to the wheel hub via a joint. The upper wishbone and the lower wishbone may be of the same length or of different lengths/sizes.

According to a further embodiment, the omnidirectional wheels are formed by mecanum wheels. These are suitable for very particularly precise millimeter-accurate maneuverability of the device in all directions.

DETAILED DESCRIPTION

Figure 1:
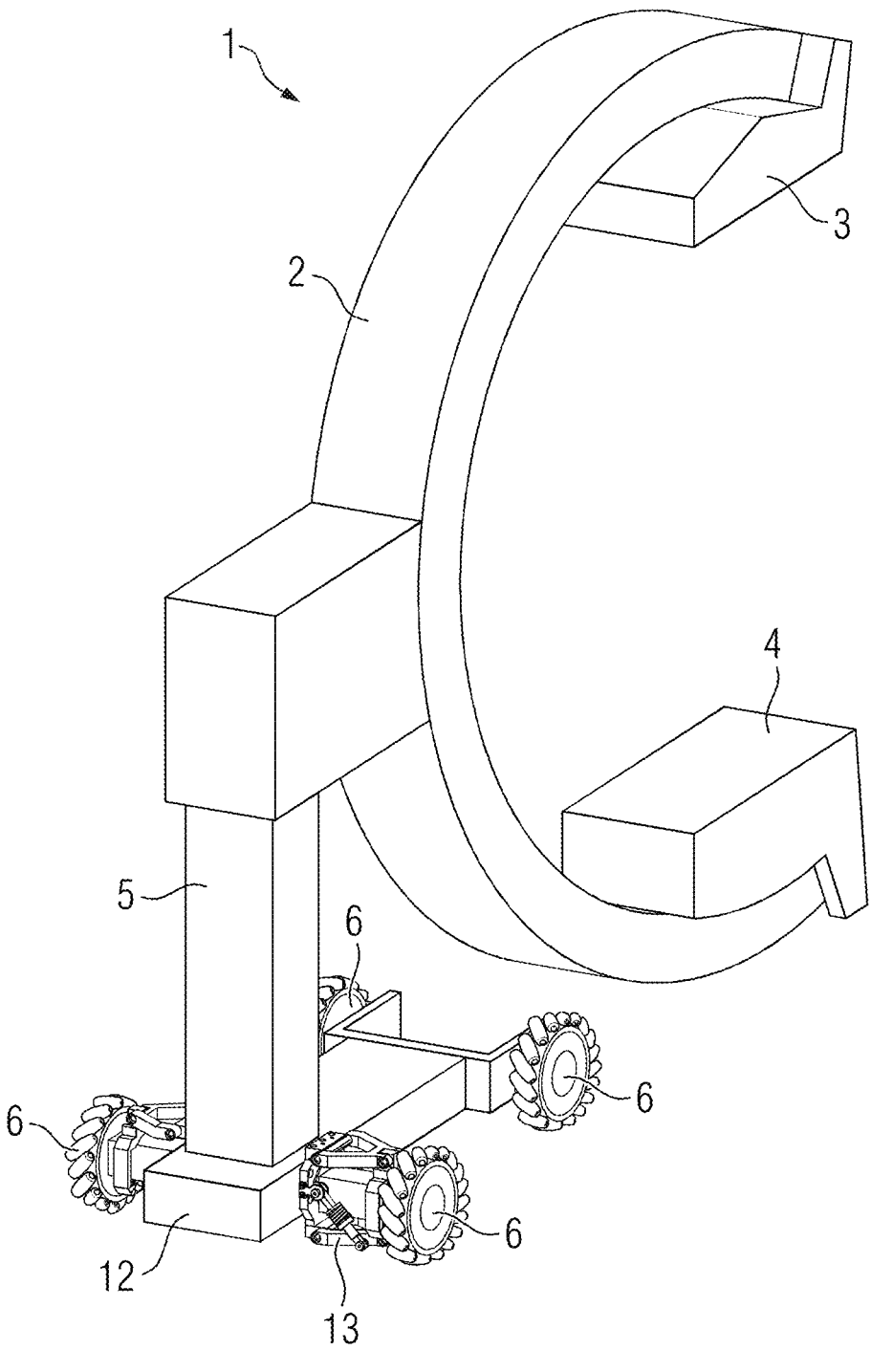
FIG. 1 is a view of one embodiment of a mobile C-arm X-ray device with omnidirectional wheels and double wishbone wheel suspensions.

FIG. 1 shows one embodiment of a mobile C-arm X-ray device 1 with a holder of a recording system in the form of a C-arm 2 arranged on a device carrier 5. The C-arm 2 holds an X-ray source 4 and an X-ray detector 3 for recording X-ray images of an object under examination at opposite ends in each case. The C-arm 2 may be adjustable at various angles and directions (e.g., horizontal, vertical, orbital) relative to the object under examination via various mountings and joints. The device carrier 5 has a chassis 12 with four omnidirectional wheels 6 (e.g., mecanum wheels) by which the device carrier 5 may be moved on the ground in all possible directions (e.g., right, left, diagonal, rotation). Omnidirectional wheels 6 have multiple rollers on their running surface; as a result of this, the running surface itself is not completely flat. Two of the four omnidirectional wheels 6 are connected to the chassis 12 via a double wishbone wheel suspension 13 in each case. These are, for example, the rear two wheels, which are opposite to each other in terms of their axis. The double wishbone wheel suspensions 13 enable the omnidirectional wheels 6 to be precisely guided and reliably held on the ground with the entire running surface, thus achieving high stability of the device carrier.

Figure 2:
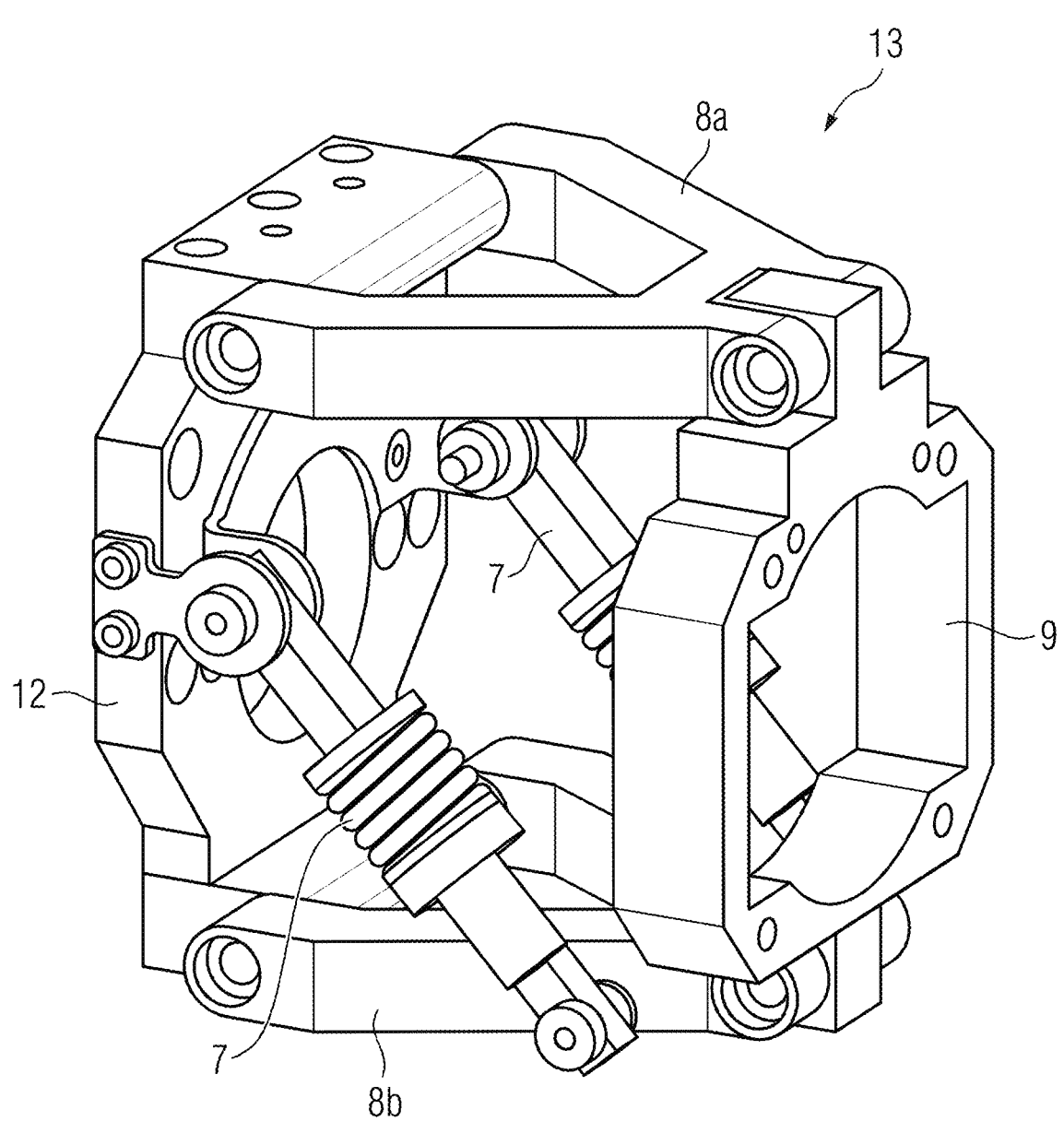
FIG. 2 is a perspective view of one embodiment of a double wishbone wheel suspension.

FIG. 2 shows a single double wishbone wheel suspension 13 in detail. The single double wishbone wheel suspension 13 includes two wishbones, one of which is an upper wishbone 8a and the other of which is a lower wishbone 8b. This makes the suspension rigid against longitudinal forces. The two wishbones 8a, 8b are, for example, each connected to the chassis 12 at two points and may have an articulated connection to the wheel hub 9 of the wheels 6. The connections may be flexible and/or articulated connections. The wishbones 8a, 8b are, for example, configured in an A-shape. The double wishbone wheel suspension 13 also has two spring suspension elements 7 that connect the chassis 12 to the lower wishbone 8b and are suitable for shock absorption. The two spring suspension elements 7 may, for example, be in the form of springs (e.g., helical springs or torsion-bar springs) or may be formed from a flexible material (e.g., rubber) or effect another type of spring suspension.

Figure 4:
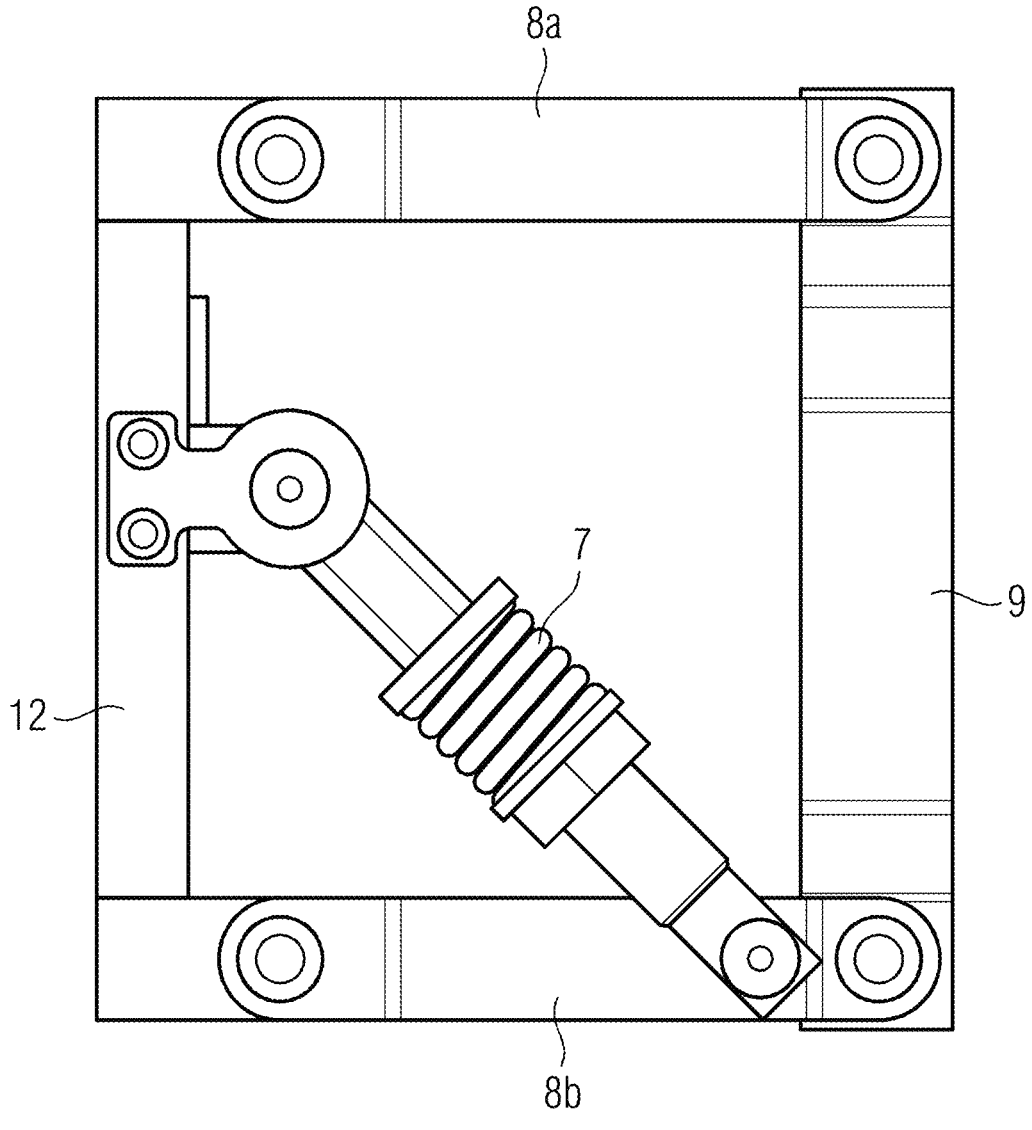
FIG. 4 is a side view of one embodiment of a double wishbone wheel suspension.
Figure 5:
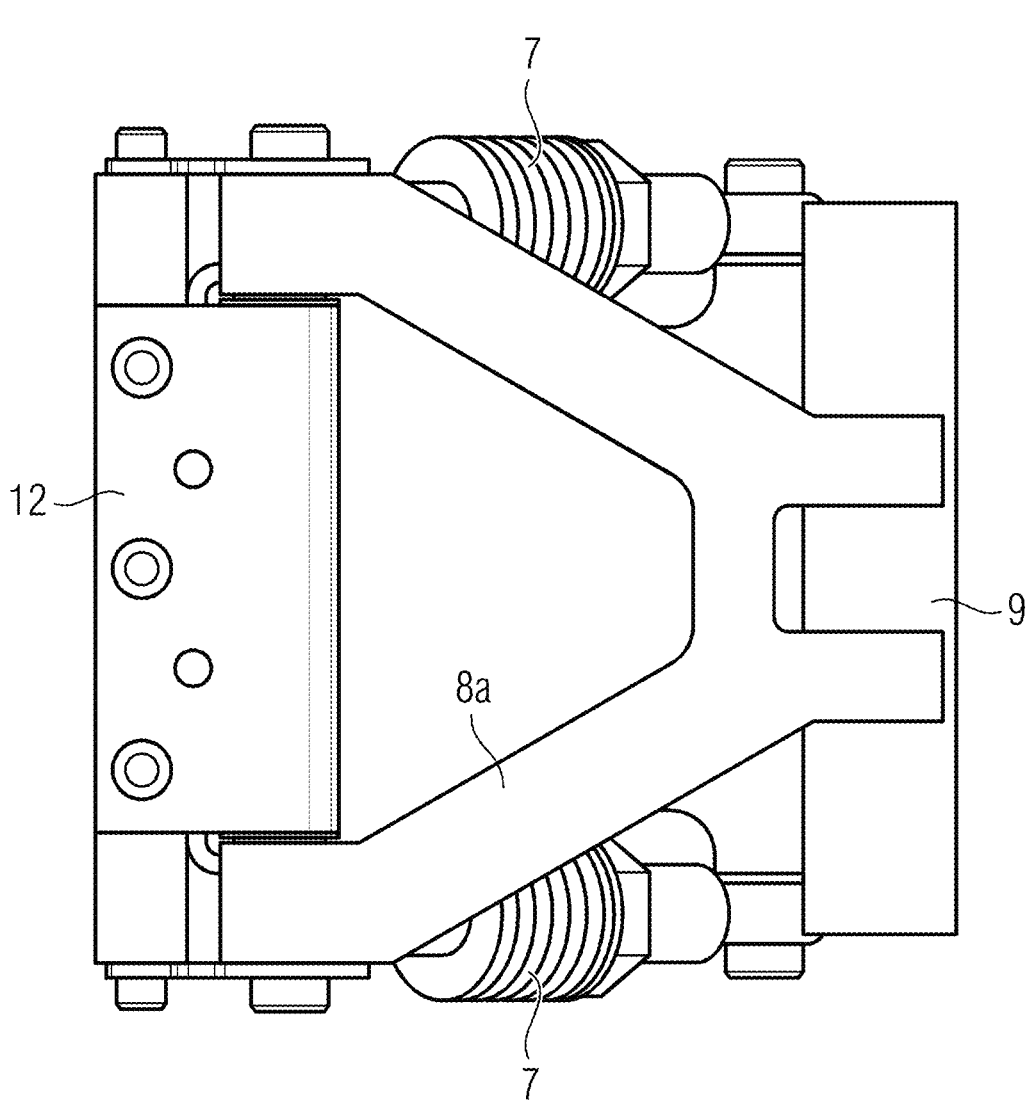
FIG. 5 is a further view from above of one embodiment of a double wishbone wheel suspension.

FIG. 4 shows a side view of one embodiment of the double wishbone wheel suspension 13. As shown in FIG. 4, the two wishbones 8a 8b may be parallel to one another (e.g., in idle state). FIG. 5 shows the double wishbone wheel suspension 13 from above so that, for example, the upper wishbone 8a, its two connections to the chassis 12, and the articulated connection to the wheel hub 9 may be identified.

Figure 3:
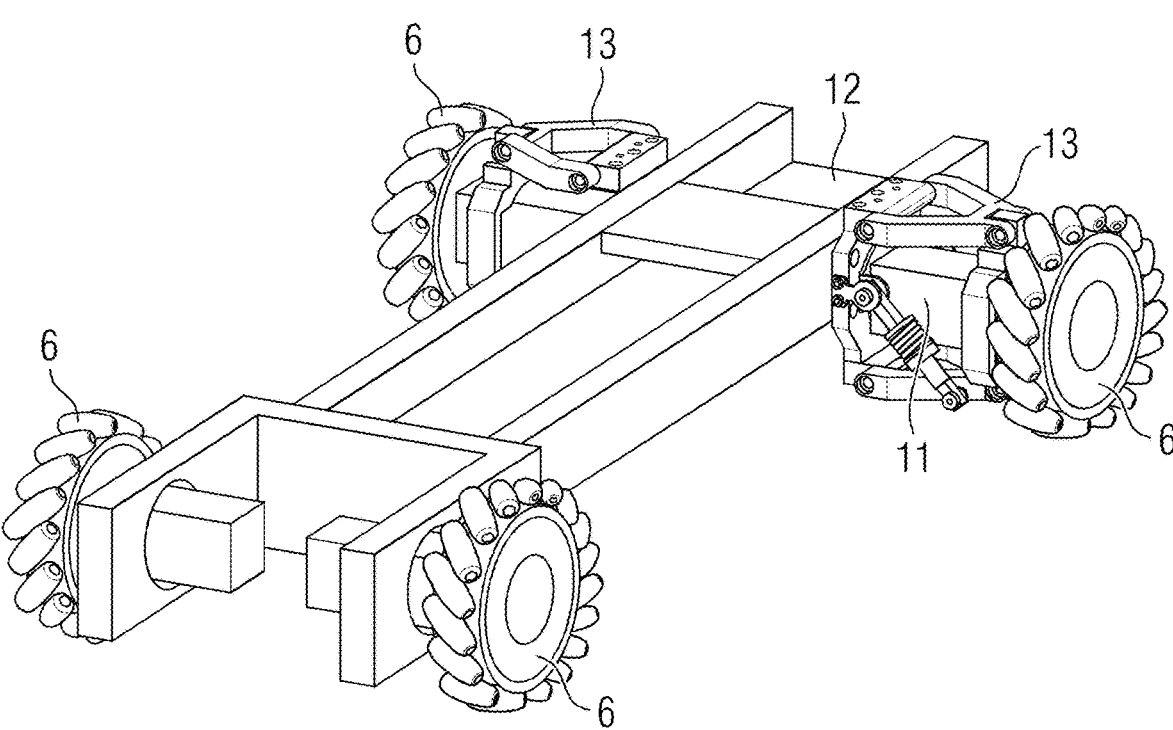
FIG. 3 is a view of one embodiment of a chassis with four omnidirectional wheels and two double wishbone wheel suspensions.

FIG. 3 shows the chassis 12 of the device carrier 5 with four omnidirectional wheels 6 and two double wishbone wheel suspensions 13 for the two rear wheels 6. The motor 11 of the respective omnidirectional wheel may, for example, be arranged in the region between the wishbones 8a, 8b.

The two wishbones 8a, 8b allow movement in the vertical direction, and the spring suspension elements 7 exert a force on the wheel in the direction of the ground in order to keep the wheel on the ground. This also works on uneven ground (e.g., very uneven ground), so that constant contact between the wheels 6 and the ground is provided. There is no tilting of the wheel that would cause the wheel rollers to no longer reliably rest completely on the ground; instead, the entire width of the running surface of the wheel is in contact with the floor. The double wishbone wheel suspension 13 enables the omnidirectional wheels, which is to be able to be driven continuously, to exert precise movements in all directions even on very uneven ground due to the constant contact with the floor.

The omnidirectional wheels are, for example, formed by mecanum wheels. Mecanum wheels are constructed such that a plurality of rollers are arranged on their circumference (e.g., running surface; at an angle of 45° to the axis of the wheel) and establish contact with the floor. The mecanum wheel is driven by a motor with a variable rotational direction and variable rotational speed (see, for example, https://en.wikipedia.org/wiki/mecanum_wheel).

In one embodiment, all four wheels each have a double wishbone wheel suspension 13. This, for example, provides good maneuverability with mecanum wheels, since all four wheels are always in contact with the floor, even on very uneven ground.

Alternatively, the mobile medical device may also have only three wheels (e.g., in an arrangement with two rear omnidirectional wheels and one central front (omnidirectional or conventional) wheel). In one embodiment, more than four wheels may be provided (e.g., six omnidirectional wheels).

The medical device may alternatively be formed by a mobile X-ray device, a device trolley, a mobile computed tomography scanner, a mobile ultrasound device, or another mobile medical device.

The present embodiments may be briefly summarized as follows: for particularly good maneuverability, a mobile medical device is provided with a device carrier. The device carrier has at least three (e.g., four) wheels, of which at least two are motor-driven omnidirectional wheels each including a motor. At least two of the omnidirectional wheels are arranged in pairs on opposite sides of a chassis of the device carrier using a wheel suspension in each case. The wheel suspensions are configured as movable perpendicularly to the ground and rigid against longitudinal forces. The wheel suspensions are, for example, formed by double wishbone wheel suspensions.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A mobile medical device comprising:
    a device carrier comprising:
        a chassis; and
        four motor-driven omnidirectional wheels,
    wherein two of the motor-driven omnidirectional wheels are arranged in a pair on opposite sides of the chassis of the device carrier using a wheel suspension in each case,
    wherein the wheel suspensions are formed by double wishbone wheel suspensions, and
    wherein two of the four motor-driven omnidirectional wheels are arranged in a pair on opposite sides of the chassis of the device carrier using a double wishbone wheel suspension.

2. The mobile medical device of claim 1, wherein each of the wheel suspensions has at least one spring suspension element.

3. The mobile medical device of claim 2, wherein each of the wheel suspensions has two spring suspension elements.

4. The mobile medical device of claim 3, wherein the spring suspension elements are formed by springs.

5. The mobile medical device of claim 2, wherein the spring suspension elements are formed by springs.

6. The mobile medical device of claim 2, wherein the motor-driven omnidirectional wheels are formed by mecanum wheels.

7. The mobile medical device of claim 1, wherein each of the wheel suspensions has at least one spring suspension element.

8. The mobile medical device of claim 7, wherein the motor-driven omnidirectional wheels are formed by mecanum wheels.

9. The mobile medical device of claim 1, wherein the mobile medical device is configured as a mobile C-arm X-ray device.

10. The mobile medical device of claim 1, wherein the mobile medical device is configured as a mobile C-arm X-ray device.

11. The mobile medical device of claim 1, wherein the double wishbone wheel suspensions in each case have an upper wishbone and a lower wishbone arranged parallel to one another.

12. The mobile medical device of claim 1, wherein the motor-driven omnidirectional wheels are formed by mecanum wheels.

\* \* \* \* \*